Figure 1:
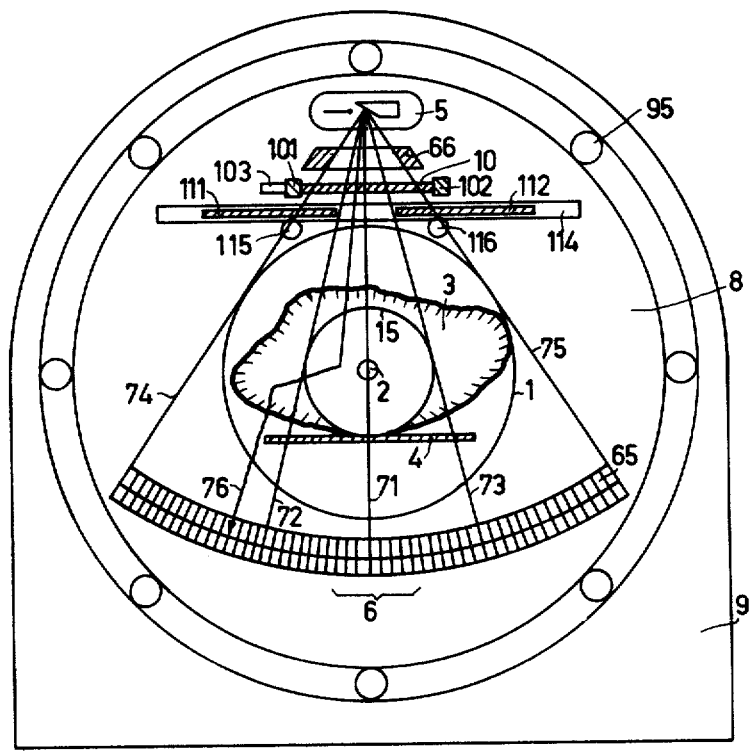

United States Patent [19]

Wagner

[11] 4,371,976
[45] Feb. 1, 1983

[54] X-RAY APPARATUS FOR DETERMINING THE ABSORPTION DISTRIBUTION IN A FLAT EXAMINATION ZONE

[75] Inventor: Wolfgang Wagner, Hamburg, Fed. Rep. of Germany

[73] Assignee: U.S. Philips Corporation, New York, N.Y.

[21] Appl. No.: 149,782

[22] Filed: May 14, 1980

[30] Foreign Application Priority Data

May 18, 1979 [DE] Fed. Rep. of Germany ....... 2920051

[51] Int. Cl.³ .................... G21K 1/04; G01N 23/08
[52] U.S. Cl. ................... 378/16; 378/152; 378/147
[58] Field of Search .............. 250/445 T, 511, 513, 250/505, 512, 510

[56] References Cited

U.S. PATENT DOCUMENTS

| 4,114,041 | 9/1978 | Oliver | 250/445 T |
| 4,145,610 | 3/1979 | Perilhou | 250/445 T |
| 4,181,858 | 1/1980 | Moore | 250/510 |
| 4,286,156 | 8/1981 | Wagner | |

FOREIGN PATENT DOCUMENTS 2609925 9/1977 Fed. Rep. of Germany .
1579694 11/1980 United Kingdom .

*Primary Examiner*—Eugene La Roche
*Assistant Examiner*—Carolyn E. Fields
*Attorney, Agent, or Firm*—Jack E. Haken

[57] ABSTRACT

The invention relates to a computer tomography apparatus for determining the absorption distribution in a relevant zone of a body, this zone being irradiated by unattenuated radiation, while the part of the body which is situated outside this zone is irradiated at the most by attenuated radiation. The radiation outside the relevant zone is attenuated in accordance with the invention by means of absorber pieces which are moved to and fro during an examination in a direction parallel to the rotary shaft around which the X-ray source is rotated. As a result, the intensity of the radiation is modulated in the time outside the zone, so that on average it is attenuated, without giving rise to hardening effects.

4 Claims, 6 Drawing Figures

X-RAY APPARATUS FOR DETERMINING THE ABSORPTION DISTRIBUTION IN A FLAT EXAMINATION ZONE

The invention relates to an X-ray apparatus for determining the absorption distribution in a flat examination zone which is situated within a body, said device comprising an X-ray source which is rotatable around an axis extending transversely of the examination zone and which comprises a diaphragm device for forming a flat, fan-shaped X-ray beam which passes through a positioning zone which encloses the examination zone, the body being arranged within the positioning zone during an examination, a detector device for measuring the radiation at the side of the positioning zone opposite the X-ray source, and an attenuation device which is connected to the X-ray source and which attenuates the radiation outside the examination zone. The fact that the diaphragm device, or the attenuation device, is connected to the radiation source does not necessarily mean that a rigid connection is concerned. It is only important that they are rotated around the axis together with the radiation source.

German Offenlegungsschrift No. 26 09 925 describes a device of the kind set forth in which the attenuation device consists of two attenuation bodies which attenuate the X-rays passing through the positioning zone outside the examination zone, but which do not completely suppress this radiation, so that the absorption can also be measured on either side of the examination zone (if the radiation were fully suppressed at these areas, the absorption in this zone could not be determined, so that the aborption distribution in the examination zone could not be reconstructed either).

In an apparatus of this kind, the dose administered to the patient is substantially reduced, whilst the absorption distribution in the examination zone (the circular zone which is irradiated from all directions by unattenuated X-rays) can be fully reconstructed.

It is drawback of the known device that the radiation attenuated by the attenuation body becomes harder with respect to the non-attenuated radiation passing through the examination zone (i.e. in the emitted X-ray spectrum, the spectral parts of greater wavelength are attenuated more than the spectral parts of smaller wavelength), thus necessitating an additional correction for accurate determination of the absorption distribution in the examination zone. It is a further drawback that detector elements which detect the radiation attenuated by the attenuation body also measure the scattered radiation generated in the examination zone; the scattered radiation measured by a detector element may be even approximately equal to the attenuated useful radiation passing through the attenuation body and measured by this detector element. As a result, large errors occur in the reconstruction of the absorption distribution outside the examination zone; these errors also have an effect on the accuracy of the reconstruction of the absorption distribution within the examination zone. The inaccuracies thus formed cannot be corrected, because the magnitude of the scattered radiation component cannot be measured.

The invention has for its object to provide an X-ray apparatus of the described kind in which the described hardening effects do not occur and in which the effect of the scattered radiation can be measured. To this end, a first X-ray apparatus in accordance with the invention is characterized in that the attenuation device comprises one or more absorber pieces which intercept X-rays and which comprise edges, directed transversely of the rotary shaft, and can be moved by a drive device in synchronism with the rotary movement of the X-ray source, parallel to the rotary shaft and in an oscillating manner, so that a part of the detector device which measures radiation outside the examination zone is fully shielded by the absorber pieces during one movement phase thereof, and is partly exposed to radiation during another movement phase of the absorber pieces.

A second X-ray apparatus in accordance with the invention is characterized in that the attenuation device comprises one or more absorber pieces which intercept X-rays and which comprise edges which are directed transversely of the rotary shaft, the X-ray source being an X-ray tube comprising an anode and a cathode for generating an electron beam which is incident on the anode in a location which forms the focus of the X-ray beam, said focus being moved to and fro, parallel to the rotary shaft and in an oscillating manner, by means of a deflection device which influences the electron beam so that a part of the detector device which measures the radiation outside the examination zone is shielded by the absorber pieces during one movement phase of the focus, and is partly exposed to radiation during another movement phase.

Both solutions have a common aspect in that only a small, continuously changing part of the effective measuring surface of the detector elements which determine the radiation outside the examination zone is exposed to unattenuated radiation. Thus, in both cases a relative movement takes place between the attenuation device and the focus of the X-ray beam in the direction parallel to rotary shaft, the attenuation device being displaced in the first case whilst the focus is displaced in the second case. The magnitude of the measuring surface exposed to radiation then amounts to a varying fraction of the total measuring surface of each detector element, whilst the body is irradiated with an intensity which varies accordingly, the mean radiation dose amounting to only a fraction of the radiation dose in the examination zone. The body of the patient is thus exposed to a reduced dose outside the examination zone, but the hardening effects occurring in the known X-ray apparatus are avoided in that the transmitted part of the fan-shaped radiation beam is unattenuated and hence exhibits the same spectrum as the part which passes through the examination zone.

During the movement phases of the absorber pieces or the focus of the X-ray beam during which the detector elements measuring the radiation outside the examination zone are completely shielded, the detector elements still produce measuring values which are not zero. This is caused by the scattered radiation which is generated in the body of the patient to be examined, positioned in the positioning zone, by the incident radiation. These scattered radiation measuring values can be used for the subsequent reconstruction of the absorption distribution in order to suppress the effect of the scattered radiation. These values are then subtracted from the measuring values each time produced by the same detector elements during a phase during which these detector elements are not completely shielded by the absorber piece or absorber pieces. The correction is accurate only if the scattered radiation is approximately equally large during both measurements. This condition is satisfied if the radiation source is rotated through only a comparatively small angle during the interval between the two measurements; this means that the period of the oscillating movement of the absorber piece or the focus of the X-ray beam should be small in comparison with the period of the rotary movement of the X-ray source (this is the period of time required by the X-ray source for one complete revolution, through 360°, around the positioning zone).

For the reconstruction of the absorption distribution on the basis of the measuring values obtained by means of an apparatus in accordance with the invention, the fact should be taken into account that the intensity of the radiation which enters the positioning zone and which does not pass through the examination zone is not constant but varies in the time in accordance with the position of the rims of the absorber pieces or of the focus. If the displacement of the absorber pieces or the focus is in synchronism with the rotary movement of the radiation source, a defined position of the absorber pieces or of the focus is associated with each angular position of the radiation source, so that in any angular position of the radiation source the part of the measuring surfaces of the detector elements which is exposed to radiation and which is more or less shielded by the attenuation device can be determined, and hence also the intensities of the radiation.

The movement need not necessarily be synchronized. For example, asynchronous movement would be permissible if there were provided, for example, a reference detector which measures the instantaneous X-ray intensity.

A simple embodiment of an X-ray apparatus in accordance with the invention is characterized in that the absorber pieces are cylindrical pieces having a cross-section which is not circular, the axes thereof being directed transversely of the rotary shaft, the drive device rotating the absorber pieces around their axes. The absorber pieces may then be directly coupled to a constant-speed drive motor.

The invention will be described in detail hereinafter, by way of example, with reference to the accompanying diagrammatic drawing.

Figure 2:
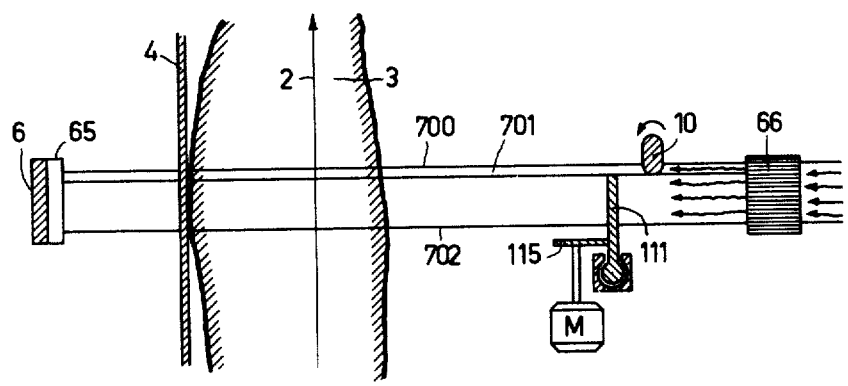
Figure 3:
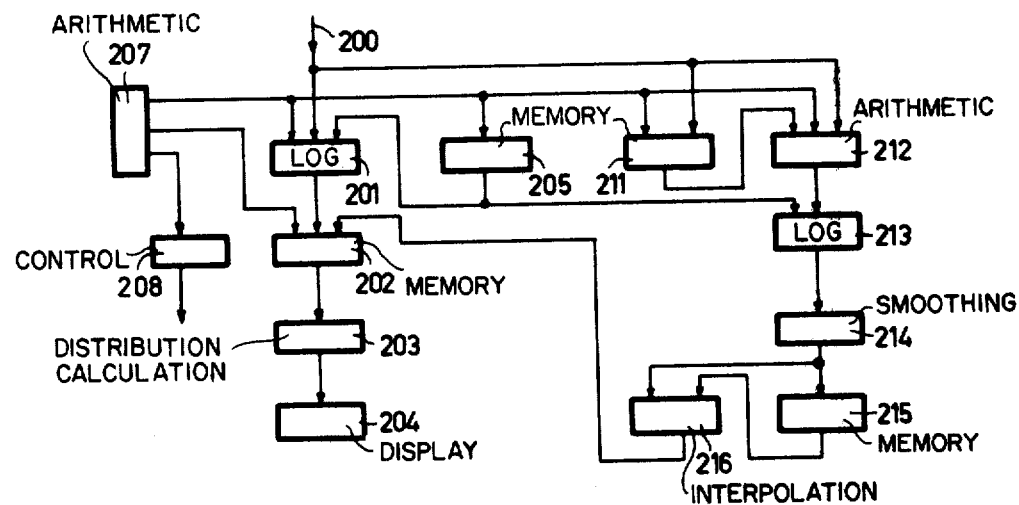
Figure 4:
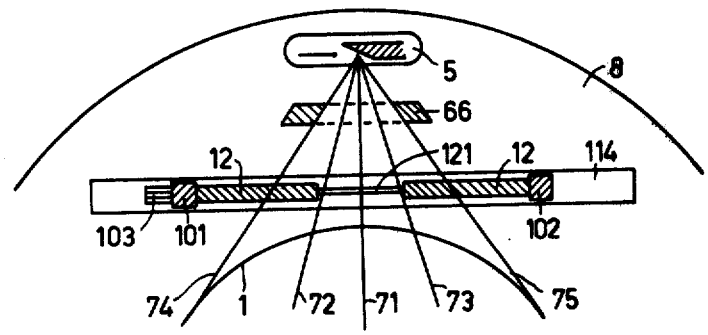
Figure 5:
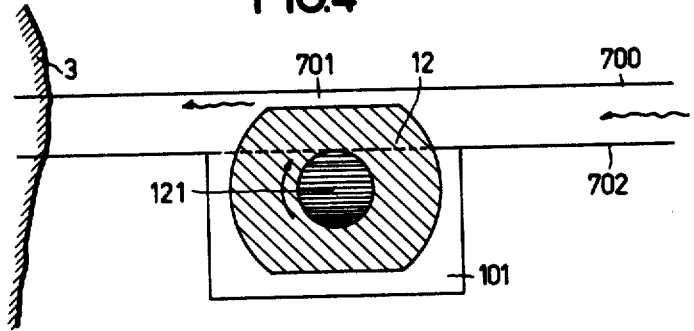
Figure 6:
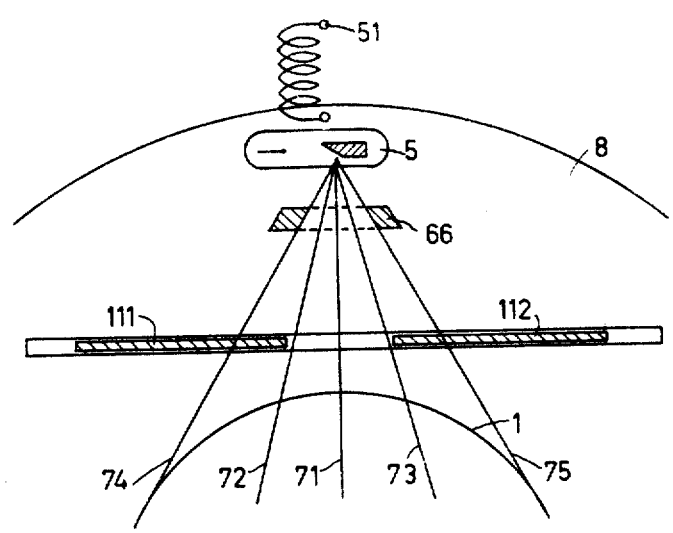

FIG. 1 shows an X-ray apparatus in accordance with the invention,

FIG. 2 is a sectional view of such an apparatus, taken perpendicularly to the plane of examination, FIG. 3 shows a block diagram of a device for determining the absorption distribution from the measuring values obtained by means of an apparatus as shown in FIG. 1, FIG. 4 is a partial front view of a further embodiment, FIG. 5 is a sectional view, taken in a plane perpendicularly to the plane of examination, of this embodiment, and FIG. 6 shows an embodiment in which the position of the focus can be changed in the direction parallel to the rotary shaft of the X-ray source.

FIG. 1 is a diagrammatic sectional view of an X-ray apparatus in accordance with the invention, the plane of the drawing being parallel to the plane of examination. The apparatus comprises a frame 9 in which an annular support 8 is journalled to be rotatable on rollers 95 around a shaft 2 which is at the same time the symmetry axis thereof. On the annular support 8 there is mounted an X-ray tube 5 and, opposite the X-ray tube, a detector device 6 which consists of a multitude of separate detector elements which are arranged on an arc of a circle. In front of the detector device 6 there is arranged a scattered radiation grid 65. The detector elements, or the centres thereof, on the one side and the X-ray tube 5 on the other side are situated in a common plane which is directed transversely of the rotary shaft 2.

In the vicinity of the X-ray source 5 there is arranged a diaphragm device 66 which stops the radiation emitted by the X-ray source in order to form a fan-shaped radiation beam, the extreme rays 74 and 75 of which are intercepted by the outer elements of the detector device 6 and are tangent to a positioning zone 1 which is concentric with respect to the rotary shaft 2. The positioning zone 1 is identical to the circular opening of the support 8. During an examination, the body of the patient 3 is situated within this positioning zone 1 on an examination table 4.

The X-ray tube 5 is used in a pulsating manner, i.e. in each angular position the tube emits a brief but strong X-ray pulse, the duration of which is small in comparison with the period of time expiring during the rotation of the annular support 8 from one angular position to the next angular position. This means that during an X-ray pulse the entire device, including the absorber pieces in accordance with the invention, may be considered to be stationary.

In accordance with the invention, in the beam path between the diaphragm device 66 and the positioning zone 1 there are arranged, symmetrically with respect to the central ray 71 (which is the connecting line between the focus of the X-ray source 5 and the rotary shaft 2), two elongate absorber pieces 111 and 112 which intercept the incident radiation. The absorber pieces 111 and 112 are not displaced during the rotation of the radiation source around the rotary shaft 2. The extreme rays 72 and 73 which pass the facing edges which are directed transversely of the plane of the drawing are tangent to a zone 15 which is concentric with respect to the rotary shaft 2 and whose radius is smaller than that of the positioning zone. This zone, referred to hereinafter as the examination zone, is exposed to unattenuated radiation in all rotary positions of the system formed by the radiation source and the detector device. The absorption distribution in the examination zone 15 can be accurately reconstructed if the absorption distribution outside the examination zone 15, but within the positioning zone 1, is also at least approximately known.

In the direction parallel to the rotary shaft, i.e. perpendicular to the plane of the drawing, the absorber pieces 111 and 112 are arranged and proportioned so that a part of the radiation emitted by the X-ray source 5 between the extreme rays 74 and 72, and 73 and 75, respectively, passes the edges of the absorber pieces, (extending parallel to the plane of the drawing (perpendicularly to the rotary shaft 2), travels through the positioning zone 1 and reaches the detector device 6. This is because the radiation beam transmitted by the diaphragm 66 has a thickness of a few millimeters (consequently, the plane of the examination zone or the positioning zone is not a geometrical plane, but a flat zone having a finite thickness) as shown in FIG. 2 in which the front and the rear boundary plane of the fan-shaped radiation beam are denoted by the references 700 and 702, respectively. In FIG. 2, the thickness of the radiation beam, that is to say the distance between the lines 700 and 702, is shown in exaggerated form in comparison with the distance between the diaphragm device 66 and the detector device 6 for the sake of clarity; in practice, the thickness of the stopped radiation beam is small in comparison with the distance between the diaphragm device and the detector device. The absorber pieces 111 and 112 extend between the extreme rays 72 and 74 and 73 and 75, respectively, so far into the radiation beam stopped by the diaphragm device 66 that they intercept almost the full radiation. It is only in a zone 701, whose thickness is small in comparison with the thickness of the radiation beam (distance between the lines 700 and 702) and which amounts to, for example, 10% of this thickness, that the radiation can pass through the body 3 beyond the edge of the absorber piece 111 in order to reach the detector device 6.

In this zone, however, there is arranged a rotatable absorber piece 10 which is journalled at 101 and 102 and which can be rotated by means of a motor 103 around its longitudinal axis which extends perpendicularly to the rotary shaft 2. The cross-section of the absorber piece 10 corresponds to a circle, on two opposite sides of which two equally large arcs of a circle amounting to approximately 90° are replaced by straight lines as shown in FIG. 2. The absorber piece 10 is arranged in the part 701 of the radiation beam which is not stopped by the new absorber pieces 111 and 112, so that it fully absorbs the radiation in the zone 701 when its flat sides are parallel to the rotary shaft 2 of the X-ray source and completely transmits the radiation in the zone 701 when it has been rotated through 90° with respect to the former position, its flat sides then extending perpendicularly to the rotary shaft 2 (and parallel to the rays 700 and 702.

When the motor 103 driving the absorber piece 10 is synchronized with the rotary movement of the source so that the absorber piece 10 is rotated through 90° between the adjacent angular positions of the radiation source which serve each time for the measuring of a set of measuring values and which are spaced, for example, 1° or less apart, the detector elements of the detector 6 which are situated between the rays 72 and 74, and 73 and 75 are completely shielded from the direct X-rays in the position of the absorber piece 10 shown in FIG. 2, whilst in the subsequent angular position they are exposed to radiation passing the edge of the absorber piece 111 in the zone 701. Even though these detector elements are not exposed to direct X-rays in one angular position, they supply a measuring value due to the multiple scattering of the X-rays in the body 3, as denoted by the ray 76 in FIG. 1. Because the scattered radiation varies only slowly in space, it may be assumed that in the next angular position of the X-ray source, in which each detector element is additionally exposed to the radiation in the zone 701, the scattered radiation component is the same for each detector element as in the preceding angular position. This fact can be used for reducing the error due to the scattered radiation effect during the reconstruction of the absorption distribution.

In FIG. 1 the examination zone 15 is concentric to the positioning zone 1. However, it may be advantageous to move the examination zone 15 with respect to the body 3 or to the positioning zone 1 and to make its magnitude adjustable in accordance with the wishes of the examiner. In that case the extreme rays 72 and 73 perform a tilting movement relative to the central ray 71 during the rotary movement of the radiation source 5. The absorber pieces 111 and 112 should then be independently displaceable perpendicularly to the central ray 71. To this end, they are arranged to be displaceable in a guide rail which extends in this direction and they can be displaced in the longitudinal direction by means of a drive roller 115, 116, respectively, coupled to a motor (FIG. 2).

FIG. 3 shows an arithmetic device for executing the reconstruction of the absorption distribution in the examination zone 15 (and possibly in the positioning zone 1), said unit being capable of processing the measuring values supplied by an apparatus as shown in FIG. 1. The measuring values supplied by the individual detector elements in each angular position of the radiation source are applied from an intermediate memory (not shown), via a line 200, to a logarithmation unit 201 which determines the absorption along the beam path through the positioning zone followed by the beam incident on the relevant object by logarithmation of the quotient of the intensity of the X-rays measured behind the positioning zone by the relevant detector element and the primary intensity, i.e. the intensity prior to the passing through the positioning zone. It is to be noted that in the device in accordance with the invention the primary intensity is not constant but fluctuates, because the part of the radiation transmitted by the diaphragm device 66 is continuously varied in dependence of the rotary position of the absorber piece 10, and also somewhat in the examination zone, that is to say between the extreme rays 72 and 73. The values of this primary intensity must be determined by calibration measurements and are stored in the memory 205 wherefrom they are applied to the logarithmation unit 201.

The influencing of the primary intensity in the examination zone can be avoided by using two separately rotatable absorber pieces instead of one such piece, said pieces reaching just as far as the extreme rays 72 and 73. However, electrical or mechanical devices must then be provided to ensure that these two absorber pieces move in synchronism. Another possibility of avoiding the modulation of the irradiated layer thickness by the absorber piece 10 consists in the reduction of the diameter of the zone present between the extreme rays 72 and 73, so that the edges thereof never extend as far as into the radiation beam in this zone (between the lines 700 and 702, FIG. 2).

In the device shown in FIG. 3, the measuring values from the detector elements which are situated between the extreme rays 72 and 73 are applied to the logarithmation unit 201, and the measuring values from the detector elements which are situated between the extreme rays 72 and 74, and 73 and 75 are applied to a memory 211 or an arithmetic unit 212. If the examination zone is concentric to the rotary shaft 2, a part of the detector elements of the detector device always measures only the radiation between the extreme rays 72 and 73, whilst the other part measures the radiation beyond these extreme rays. However, if the examination zone 15 is not concentric with respect to the rotary shaft 2, a part of the detector elements measures the radiation passing through the examination zone during one phase of the examination, whilst in another phase they measure the radiation passing through the positioning zone outside the examination zone. Therefore, there is provided an arithmetic device 207 which, for each angular position of the source, calculates which detector elements measure each time the radiation within the examination zone and which detector elements measure the radiation outside the examination zone, and which controls the devices 201, 205, 211 and 212 accordingly. Moreover, the arithmetic device 207 controls a control member 208 which influences the drive for the rollers 115 and 116 for adjustment of the absorber pieces 111 and 112 so that they are arranged in the previously calculated position.

The measuring values supplied by detector elements between the extreme rays 72 and 74, and 73 and 75 and measured in an angular position of the X-ray source in which the area outside the examination zone was completely shielded (i.e. in the position of the absorber piece 10 shown in FIG. 2) are a measure for the scattered radiation. These measuring values are stored in the intermediate memory 211. The measuring values supplied by these detector elements in the subsequent angular position of the X-ray source, however, are a measure for the absorption the as well as the scattered radiation contribution, as has already been described. These measuring values are applied to the arithmetic device 212 which subtracts therefrom the scattered radiation component stored in 211, so that the output signals of the arithmetic device 212 correspond to the absorption values of the body outside the rays 72 and 73 (FIG. 1) wherefrom the scattered radiation component has been removed. The logarithm of the values of the primary intensity, derived from the intermediate memory 205, is determined in the arithmetic device 213, these values being subjected to a smoothing operation in a subsequent arithmetic unit 214 in order to reduce the effect of the noise caused by the reduced effective X-ray intensity outside the examination zone 15. This smoothing operation has no substantial effect on the determination of the absorption distribution in the examination zone 15, but improves the image quality of the measured absorption distribution outside the examination zone.

The measuring values which represent only the scattered radiation component and which are stored in the intermediate memory 211 are not conclusive as regards the absorption. For the reconstruction of the absorption distribution in the zone outside the examination zone, use should only be made of measuring values which contain a component corresponding to the absorption in addition to the scattered radiation component. Therefore, measuring values for the absorption are lacking and these measuring values are determined, in the arithmetic unit 216, by interpolation from the measuring values correctly supplied by the device 214 and from the measuring values stored in the memory 215 and supplied by the same or a neighbouring detector element. Subsequently, these values are stored in the memory 202, together with the measuring values associated with the examination zone and logarithmated in 201, after which the absorption distribution is calculated in the customary manner in the arithmetic unit 203 and can be displayed on a display device 204.

FIGS. 4 and 5 show a part of a further embodiment of an X-ray apparatus. Two absorber pieces 12 are arranged on a shaft 121 which is present between the diaphragm device 66 and the positioning zone 1 and which extends perpendicularly to the rotary shaft 2 and adjacent the radiation beam transmitted by the diaphragm device 66. The shaft 121 is journalled at 101 and 102 and is driven by a motor 103 which is synchronized with the rotary movement of the radiation source 5 and the annular support 8 around the shaft 2 as described with reference to the FIGS. 1 to 3. The absorber pieces 12, wherebetween an area on the shaft 121 remains free so that the radiation can pass in an unobstructed manner through this zone defined by the rays 72 and 73, have a cross-section similar to that of the absorber piece 10 in the embodiment described with reference to the FIGS. 1 and 2. They can be made, for example, from a circular-cylindrical absorber piece by machining down two opposite, parallel sides. In the position of the absorber pieces shown in FIG. 5, the radiation beam formed by the diaphragm device 66 can pass the absorber pieces 12 over a part 701 of its thickness in order to reach the body 3. However, if the absorber pieces 12 are situated in a position rotated through 90° with respect to FIG. 5, in which case the two flat side faces extend perpendicularly to the examination zone, the radiation beam is fully absorbed.

When the examination zone is to be eccentrically situated with respect to the positioning zone 1, the absorber pieces should be moved together to the left or to the right out of the position shown in FIG. 4. To this end, the device may be mounted on a rail 114 which itself is displaceable in its longitudinal direction with respect to the annular support 8 in a manner not shown.

The two absorber pieces need not necessarily be interconnected by a common shaft either. Use can be made of two separate absorber pieces which are independently displaceable in the direction of the longitudinal axis and which are driven in synchronism with the rotary movement.

Other than in the described embodiments, the absorber piece may have a cross-section which comprises two opposite arcs of a circle which amount to approximately 120°, the intermediate part which each time extends over approximately 60° being flat, like in FIG. 5. When this absorber piece is rotated through 60° between two successive measuring cycles (adjacent angular positions in which each time a set of absorption data is measured), radiation reaches the part of the positioning zone 1 which is situated outside the zone 15 only every third measuring cycle, whilst during the intermediate two measuring cycles this zone remains shielded. The radiation dose is thus further reduced. However, this shielding should be taken into account for the determination of the absorption distribution by means of the device shown in FIG. 3. As a continuation of this idea, the cross-section of the absorber piece (the absorber pieces) may be shaped so that the zone outside the examination zone is exposed to radiation only every fourth or fifth measuring cycle, or even less often.

FIG. 6 diagrammatically shows a further embodiment in accordance with the invention. The device again comprises an X-ray tube 5, connected to the support 8, a diaphragm device 66 and absorber pieces 111 and 112. The absorber pieces 111 and 112 are proportioned and arranged in a direction perpendicularly to the plane of the drawing (parallel to the rotary shaft 2 not shown) so that they completely shield the zone between the extreme rays 72 and 74, and 73 and 75, but also that the two absorber pieces just fully shield the radiation beam on at least each of one of their two edges which extend parallel to the plane of examination and perpendicularly to the rotary shaft (not shown). When the focus of the X-ray source 5 is displaced perpendicularly to the plane of the drawing, the radiation beam is also shifted, so that the radiation can pass the absorber pieces 111 and 112 in the zone between the extreme rays 72 and 74, and 73 and 75. For the displacement of the focus there is provided a deflection coil 51 which is arranged so that the path followed by the electrons within the X-ray source 5 as far as the focus and the coil axis are perpendicular to each other and form a plane which extends transversely of the rotary shaft. In this configuration, the focus is shifted perpendicularly to the plane of the drawing or parallel to the rotary shaft by application of a suitable deflection current to the coil 51, the detector elements which are situated on the other side of the positioning zone 1 and which are not shown then being alternately fully shielded and at least partly exposed to radiation at the area of the radiation 72 and 74, and 73 and 75.

Even though the invention has been described with reference to an X-ray apparatus in which the system formed by the radiation source and the detector device is rotated around the rotary shaft during the measurement (so-called third-generation computer tomography), it can also be used in apparatus where the detector device is stationary and extends over an arc of a circle of approximately 360° around the rotary shaft 2 of the radiation source (fourth-generation).

What is claimed is:

1. In apparatus for determining an X-ray absorption distribution in a planar examination zone which is situated in a body, the body being disposed within a positioning zone which encloses the examination zone, of the type comprising:

X-ray source means which function to produce X-rays, diaphragm means which function to form X-rays produced by the source means into a flat fan-shaped beam which passes through the positioning zone in the plane of the examination zone, detector means situated adjacent the positioning zone which function to receive and measure X-rays in the beam which have passed through the positioning zone, positioning means which function to cause the source means to irradiate the positioning zone from a plurality of successive positions around an axis which extends through the examination zone transverse to the plane thereof, and means which function to attenuate X-rays in the beam so that the average flux of the X-rays which pass through the examination zone is greater than the average flux of the X-rays which pass through the positioning zone but which do not pass through the examination zone; the improvement wherein the means which function to attenuate comprise:

one or more absorber pieces which intercept X-rays and which define edges which are oriented transverse to the axis and means which function to move the absorber pieces in synchronism with the operation of the positioning means so that at certain of the positions around the axis the absorber pieces completely shield X-rays which pass through the positioning zone but do not pass through the examination zone from reaching the detector means and the absorber pieces only partially shield said portion of the x-ray beam at others of said positions.

2. The apparatus of claim 1 wherein the absorber pieces are cylindrical and have a cross-section which is non-circular, the axis of each absorber piece being directed parallel to the plane of the examination zone, and wherein the means which function to move the absorbing pieces rotate one or more of them about its axis.

3. The apparatus of claim 2 wherein the positioning means rotates the X-ray source means and detector means about the axis which is transverse to the examination zone and wherein the means which function to attenuate comprise further absorption pieces which are rigidly attached to the X-ray source means and which partially shield a portion of the radiation beam which does not pass through the examination zone; the portion of radiation not thus shielded by the further absorption pieces being intermittently shielded by the rotating absorber pieces.

4. In apparatus for determining an X-ray absorption distribution in a planar examination zone which is situated in a body, the body being disposed within a positioning zone which encloses the examination zone, of the type comprising:

X-ray source means which function to produce X-rays, diaphragm means which function to form X-rays produced by the source means into a flat fan-shaped beam which passes through the positioning zone in the plane of the examination zone, detector means situated adjacent the positioning zone which function to receive and measure X-rays in the beam which pass through the positioning zone, positioning means which function to cause the source means to irradiate the positioning zone from a plurality of successive positions around an axis which extends through the examination zone transverse to the plane thereof, and means which function to attenuate X-rays in the beam so that the average flux of the X-rays which pass through the examination zone is greater than the average flux of the X-rays which pass through the positioning zone but which do not pass through the examination zone; the improvement wherein the means which function to attenuate comprise one or more absorber pieces which intercept X-rays and which define edges which are oriented transverse to the axis;

the X-ray source means comprises: an X-ray tube, including an anode and a cathode for generating an electron beam which is incident on the anode at a location which forms a focus of the X-ray beam and;

means for deflecting the electron beam which function to move the focus parallel to the axis in an oscillating manner so that, at certain locations of the focus, the absorber pieces completely shield a portion of the X-ray beam which passes through the positioning zone without passing through the examination zone from the detector means while at other locations of the focus the absorber pieces only partially shield said portion of the X-ray beam from the detector.

* * * * *